United States Patent [19]

Znaiden et al.

[11] Patent Number: 5,552,148
[45] Date of Patent: Sep. 3, 1996

[54] PETROLEUM JELLY WITH INOSITOL PHOSPHATES

[75] Inventors: Alexander P. Znaiden, Trumbull; Brian Crotty, Branford; Anthony Johnson, Fairfield, all of Conn.

[73] Assignee: Chesebrough-Pond's USA Co., Division of Conopco, Inc., Greenwich, Conn.

[21] Appl. No.: 481,568

[22] Filed: Jun. 7, 1995

[51] Int. Cl.$^6$ .................................................. A61K 7/48
[52] U.S. Cl. ......................... 424/401; 514/844; 514/846; 514/847; 514/937
[58] Field of Search ........................... 424/401; 514/847, 514/844, 846, 937, 938

[56] References Cited

U.S. PATENT DOCUMENTS

| | | |
|---|---|---|
| 4,760,096 | 7/1988 | Sakai et al. . |
| 5,015,634 | 5/1991 | Siren . |
| 5,019,566 | 5/1991 | Siren . |
| 5,023,248 | 6/1991 | Siren . |
| 5,051,411 | 9/1991 | Siren . |
| 5,059,594 | 10/1991 | Sawai et al. . |
| 5,082,833 | 1/1992 | Shamsuddin . |
| 5,116,605 | 5/1992 | Alt . |
| 5,268,176 | 12/1993 | Znaiden et al. . |
| 5,300,289 | 4/1994 | Garlich et al. . |
| 5,310,556 | 5/1994 | Ziegler . |
| 5,434,144 | 7/1995 | Kasting et al. ............ 514/76 |

FOREIGN PATENT DOCUMENTS

WO90/01323  2/1990  WIPO .

Primary Examiner—Thurman K. Page
Assistant Examiner—Sharon Howard
Attorney, Agent, or Firm—Milton L. Honig

[57] ABSTRACT

A cosmetic composition is provided that includes an inositol phosphate dispersed within petroleum jelly through aid of a lipid system. The lipid system may include such components as a phosphatide, a sterol, a $C_{10}$–$C_{22}$ fatty acid and combinations thereof.

7 Claims, No Drawings

PETROLEUM JELLY WITH INOSITOL PHOSPHATES

BACKGROUND OF THE INVENTION

1. Field of the Invention

The invention relates to cosmetic compositions whose major component is petroleum jelly and which incorporates inositol phosphates.

2. The Related Art

Petroleum jelly is one of the oldest skin treatment products still in commerce today. For over 100 years, the Chesebrough Company and its successors have sold the substance under the brand, Vaseline®. There is good reason for the longevity of this product. Its occlusive and healing properties render this product especially efficacious against dry and damaged skin.

Inositol phosphate is a medicinal of more recent discovery. A wealth of literature surrounds the beneficial chemistry of inositol phosphate. Most of this literature focuses upon the medicinal aspects involving oral ingestion of the material. For instance, U.S. Pat. No. 5,051,411 (Siren) utilizes inositol phosphates to reduce the negative effects of ingested toxic metals such as lead, mercury, nickel and chromium to prevent or alleviate disorders based upon such metals. Typical disorders disclosed were immunodeficiency, hypertension and dermatitis. Related disclosures are found in U.S. Pat. No. 5,015,634 (Siren) directed at preventing or alleviating tissue damage and U.S. Pat. No. 5,019,566 (Siren) directed at treating an inflammatory condition, such as arthritis. U.S. Pat. No. 5,023,248 (Siren) describes methods for treating diabetes or its complications by administration of inositol triphosphate.

U.S. Pat. No. 5,082,833 (Shamsuddin) discloses a method for moderating the rate of cellular mitosis by treatment with inositol phosphates. Target diseases are leukemia, AIDS and fungal or protozoal infections.

U.S. Pat. No. 5,059,594 (Sawai et al.) reports the use of phytic acid and ferric ions in compositions directed at the removal of uraroma and body smell, detoxication, treatment of diabetes and hyperlipemia, remediation of erythrocyte flexibility and dysmnesia and the inhibition of the proliferation of fat cells.

A much smaller body of literature has suggested the use of inositol phosphates such as phytic acid in the cosmetics area. For instance, U.S. Pat. No. 5,116,605 (Alt) incorporates phytic acid with a variety of other substances into a composition for mitigating male pattern baldness and testosterone-induced acne. U.S. Pat. No. 5,268,176 (Znaiden et al.) reports the use of phytic acid for topical treatment of telangiectasia, a dermatological condition commonly known as spider veins. A considerable number of disclosures are related to the use of phytic acid as a dental care product, among the more recent being U.S. Pat. No. 5,300,289 (Garlich et al.).

While it is evident from the foregoing that inositol phosphates are useful in a broad range of medical treatments, knowledge about their cosmetic activities is still at a formative stage.

Delivery of inositol phosphates in a vehicle such as petroleum jelly appears to present potential for even higher levels of effectiveness than previously found with aqueous cream and lotion vehicles. Inositol phosphates are unfortunately not readily soluble or dispersable in petroleum jelly. Systems are required which can aid dispersion of these hydrophilic substances into petroleum jelly.

Accordingly, it is an object of the present invention to provide cosmetic compositions having inositol phosphates uniformly dispersed or solubilized within petroleum jelly.

Another object of the present invention is to provide cosmetic compositions with skin healing, moisturizing, conditioning, skin lightening and other improved functional activities.

These and other objects of the present invention will become more readily apparent from consideration of the following summary and detailed description.

SUMMARY OF THE INVENTION

A cosmetic composition is provided that includes:

(i) from 50% to 98% by weight of petroleum jelly;

(ii) from 0.001 to 40% by weight of inositol phosphate; and (iii) from 0.1 to 30% by weight of a lipid system.

DETAILED DESCRIPTION

Now it has been found that a cosmetic composition wherein petroleum jelly is the main component and vehicle can be formulated with the aid of a lipid system to micro disperse therein inositol phosphates. Most preferred as a lipid system are those substances selected from the group consisting of phosphatides, $C_{10}$–$C_{22}$ fatty acids, sterols and mixtures thereof. The lipid system prevents phase separation and maintains the cosmetic product in an extended state of stability.

Accordingly, a first essential element of the present invention is that of petroleum jelly. Amounts of this material may range from 50% to 98%, preferably from 60% to 95%, optimally from 75% to 90% by weight.

A second essential element of the present invention is that of an inositol phosphate. By definition an inositol phosphate is a phosphate derivative of inositol, which may be one or a combination of mono-, di-, tri-, tetra-, penta- or hexaphosphate. Inositol is also known as 1,2,3,4,5,6-hexahydroxycyclohexane and 1,2,3,4,5,6-cyclohexanehexol. Most preferred is inositol hexaphosphate, otherwise known as phytic acid. For further descriptions of these phosphates, attention is drawn to U.S. Pat. No. 5,051,411, herein incorporated by reference. Amounts of these phosphates may range anywhere from 0.001 to 40%, preferably from 0.1 to 20%, optimally from 0.5 to 10% by weight of the total composition. The relative weight ratio of petroleum jelly to inositol phosphate may range from 5000:1 to 5:1, preferably from 500:1 to 10:1, optimally from 100:1 to 40:1.

When the lipid system contains a phosphatide, it is most preferred that this be lecithin. Amounts of this material may range from 0.1 to 10%, preferably from 0.5 to 8%, optimally from 2 to 5% by weight.

Additional lipids may be included in compositions of the present invention. Particularly effective are $C_{10}$–$C_{22}$ fatty acids. Suitable fatty acids include lauryl, myristyl, cetyl, palmityl, oleoyl, stearic, isostearic and behenyl acids. Amounts of this substance may range from 0.1 to 20%, preferably from 0.5 to 10%, optimally from 1% to 6% by weight.

Other particularly effective lipids are the sterols. Illustrative sterols are those selected from soy sterol, ergosterol, stigmasterol, cholesterol, sitosterol and combinations thereof. Amounts of this material may range from 0.1 to 20%, preferably from 0.5 to 10%, optimally from 1 to 5% by weight.

Although compositions according to the present invention may be anhydrous, they usually will contain water in amounts from 0 to 15%, preferably from 0.8 to 10%, optimally from 1 to 8%, especially from 4 to 6% by weight.

Beyond the aforementioned components, the present invention may also include other ingredients typically found in cosmetic formulations. Among these ingredients are emollients, humectants, thickeners, preservatives, fragrances and vitamins.

Emollients may be selected from materials such as $C_8$–$C_{30}$ fatty alcohols, triglyceride oils, silicone oils and a variety of esters. Amounts of the emollients may range from 0.5 to 20%, preferably from 1 to 10%, optimally from 2 to 8% by weight. Illustrative emollients are stearyl alcohol, cetyl alcohol, isopropyl palmitate, isopropyl myristate, lanolin, sunflower oil, evening primrose oil, soybean oil, dimethicone, cyclomethicone, dimethicone copolyol and dimethyl polysiloxane.

Thickeners may be selected from such materials as cross-linked polyacrylates available under the Carbopol® trademark, celluloses such as sodium carboxymethylcellulose, hydroxyethylcellulose, hydroxypropylcellulose and methyl cellulose, and natural gums such as xanthan, carrageenan and pectin gums. Most preferred are the crosslinked polyacrylates, especially Carbopol 934® available from the B. F. Goodrich Company.

Powdered thickeners may be such materials as chalk, talc, Fullers earth, kaolin, starch, colloidal silica, smectites clays, montmorillonite clays and chemically modified magnesium aluminum silicates.

Among the useful preservatives are methyl paraben, propyl paraben, EDTA salts, potassium sorbate, potassium benzoate and DMDM hydantoin.

Cosmetic compositions of the present invention may also contain vitamin ingredients such as Vitamin A palmitate, Vitamin E acetate, Niacin, Vitamin C and combinations thereof.

Emulsifiers may also be useful for purposes of the present invention at levels to from 0.1 to 10% by weight. These emulsifiers may be alkoxylated $C_8$–$C_{30}$ fatty acids and fatty alcohols. Examples of such materials are polyoxyethylene (4) lauryl ether, polyoxyethylene (8) monostearate, polyoxyethylene (10) cetyl ether and polyoxyethylene (20) stearyl ether. A particularly preferred emulsifier is Myreth-3-Myristate (CTFA name) available commercially as Cetiol 1414-E®.

The following examples will more fully illustrate select embodiments of this invention. All parts, percentages and proportions referred to herein and in the appended claims are by weight of the total composition unless otherwise stated.

EXAMPLE 1

A pair of experiments were conducted to evaluate compatibility of phytic acid in petroleum jelly. The following two formulations were prepared.

TABLE I

| | FORMULATION A | |
|---|---|---|
| PHASE | COMPONENT | WEIGHT % |
| A | Petroleum Jelly | 95 |
| B | Phytic Acid* | 5 |

*50% aqueous solution pre-neutralized with 4 moles sodium hydroxide.

Procedure:

Phase A was heated to 80° C. and mixed vigorously. Phase B was added while mixing was continued. Cooling began during the last mixing step. Mixing was stopped when the batch reached room temperature.

TABLE II

| | FORMULATION B | |
|---|---|---|
| PHASE | COMPONENT | WEIGHT % |
| A | Petroleum Jelly | 81.5 |
| B | Soya Sterol | 5 |
| B | Stearic Acid | 2.5 |
| C | Lecithin | 6 |
| D | Phytic Acid* | 5 |

*50% aqueous solution preneutralized with 4 moles sodium hydroxide.

Procedure:

Phase A was heated and mixed thoroughly. Phase B was heated to 80° C. and held till fully melted. When phase B melted, phase C was slowly added. Upon phase C having melted into phase B, phase D was added and mixed thereinto. Slowly the resultant hot mixture of phase B, C and D was hot mixed with phase A. Blending continued for 15 minutes and the mixture was then allowed to cool. Cooling was discontinued when the batch reached room temperature.

Stability Tests:

Cream formulations A and B were allowed to equilibrate overnight and then placed for stability testing. These studies are recorded in the table below.

TABLE III

| | FORMULATION A | |
|---|---|---|
| TEMPERATURE STORED | 1 WEEK STORAGE | 2 WEEK STORAGE |
| 120° C. | Unstable | Unstable |
| 110° C. | Stable | Stable |
| 100° C. | Stable | Stable |
| Room Temperature | Stable | Stable |

TABLE IV

| | FORMULATION B | |
|---|---|---|
| TEMPERATURE STORED | 1 WEEK STORAGE | 2 WEEK STORAGE |
| 120° C. | Stable | Stable |
| 110° C. | Stable | Stable |
| 100° C. | Stable | Stable |
| Room Temperature | Stable | Stable |

Based on the stability results it appears that the combination of soya sterol stearic acid and lecithin provides stable dispersion of phytic acid in petroleum jelly.

EXAMPLES 2–7

The following formulas illustrate typical compositions according to the present invention.

| COMPONENT | FORMULA (WT. %) | | | | | |
|---|---|---|---|---|---|---|
| | 2 | 3 | 4 | 5 | 6 | 7 |
| Petroleum Jelly | 50 | 95 | 98 | 75 | 85 | 85 |
| Inositol Phosphate | 21 | 3 | 0.01 | 20 | 5 | 1 |
| Lecithin | 10 | 2 | 0.10 | 3 | 4 | 10 |
| Cholesterol | 10 | — | 0.10 | — | — | 1 |
| Stearic Acid | 2 | — | 1.79 | 2 | 2 | 2 |
| Water | 7 | — | — | — | 4 | 1 |

The foregoing description and Examples illustrate selected embodiments of the present invention. In light thereof, various modifications will be suggested to one skilled in the art, all of which are within the spirit and purview of this invention.

What is claimed is:

1. A cosmetic composition comprising:

(i) from 50% to 98% by weight of petroleum jelly;
   (ii) from 0.001 to 40% by weight of inositol phosphate;
   (iii) from 0.1 to 30% by weight of a lipid system; and
   (iv) from 0 to 15% by weight of water.

2. A cosmetic composition according to claim 1 wherein the lipid system comprises from 0.1 to 10% by weight of a phosphatide.

3. A cosmetic composition according to claim 2 wherein the lipid system further comprises from 0.1 to 20% by weight of a $C_{10}$–$C_{22}$ fatty acid.

4. A cosmetic composition according to claim 3 wherein the lipid system further comprises from 0.1 to 20% by weight of sterol.

5. A cosmetic composition according to claim 1 further comprising from 4 to 10% by weight of water.

6. A cosmetic composition according to claim 2 wherein the phosphatide is lecithin.

7. A method for treating skin to improve a functional activity selected from the group consisting of skin healing, moisturizing, conditioning, skin lightening and combinations thereof, by applying to the skin a cosmetic composition comprising a combination of petroleum jelly and an inositol phosphate in a weight ratio from 5000:1 to 5:1 and water in an amount from 0 to 15% by weight of the composition.

* * * * *